United States Patent
Hampp

(10) Patent No.: US 8,109,999 B2
(45) Date of Patent: Feb. 7, 2012

(54) INTRAOCULAR LENS

(75) Inventor: Norbert Hampp, Amöneburg (DE)

(73) Assignee: Norbert Hampp, Amöneburg (DE)

( * ) Notice: Subject to any disclaimer, the term of this patent is extended or adjusted under 35 U.S.C. 154(b) by 501 days.

(21) Appl. No.: 12/067,225

(22) PCT Filed: Sep. 22, 2006

(86) PCT No.: PCT/EP2006/009223
§ 371 (c)(1),
(2), (4) Date: Jul. 14, 2008

(87) PCT Pub. No.: WO2007/033831
PCT Pub. Date: Mar. 29, 2007

(65) Prior Publication Data
US 2009/0157178 A1    Jun. 18, 2009

(30) Foreign Application Priority Data

Sep. 23, 2005    (DE) .................... 10 2005 045 540

(51) Int. Cl.
*A61F 2/16*    (2006.01)

(52) U.S. Cl. .................................................. 623/6.56
(58) Field of Classification Search ............. 623/4.1, 623/5.16, 6.11, 6.22, 6.56
See application file for complete search history.

(56) References Cited

U.S. PATENT DOCUMENTS

| | | | |
|---|---|---|---|
| 2,725,377 A | 11/1955 | Brody et al. | |
| 6,887,269 B1 * | 5/2005 | Hampp et al. | 623/6.57 |
| 2005/0018310 A1 | 1/2005 | Kornfield et al. | |
| 2005/0027031 A1 * | 2/2005 | Chang et al. | 522/68 |
| 2005/0099597 A1 | 5/2005 | Sandstedt et al. | |

FOREIGN PATENT DOCUMENTS

| | | |
|---|---|---|
| WO | WO 96/10069 | 4/1996 |
| WO | WO 0135867 A2 * | 5/2001 |
| WO | WO 2004/072689 | 8/2004 |

* cited by examiner

*Primary Examiner* — William H. Matthews
(74) *Attorney, Agent, or Firm* — McGlew and Tuttle, P.C.

(57) ABSTRACT

The invention relates to an artificial intraocular lens consisting of a polymer material which permits a change of the optical properties of the artificial intraocular lens when exposed to light. This enables the lens to be exactly adjusted to the required visual acuity upon implantation thereof.

17 Claims, 3 Drawing Sheets a) head-to-tail cycloaddition b) head-to-head cycloaddition head-to-head cycloaddition head-to-tail cycloaddition

INTRAOCULAR LENS

CROSS REFERENCE TO RELATED APPLICATIONS

This application is a United States National Phase application of International Application PCT/EP 2006/009 223 and claims the benefit of priority under 35 U.S.C. §119 of German Patent Application DE 10 2005 045 540.9 filed Sep. 23, 2005, the entire contents of which are incorporated herein by reference.

FIELD OF THE INVENTION

The invention relates to an artificial intraocular lens consisting of a polymer material which permits a change of the optical properties of the artificial intraocular lens when exposed to light. This enables the lens to be exactly adjusted to the required visual acuity upon implantation thereof.

BACKGROUND OF THE INVENTION

The cataract is a collective term for diseases of the eye that involve an opacification of the originally clear eye lens. Currently, there are approximately 25 million people worldwide who have become blind due to a cataract, and at least 110 million people who suffer from a substantially impaired vision. An effective medical treatment for reversing cataract formation is currently not available. Therefore, the usual treatment of a cataract is to surgically remove the cloudy lens and to implant an artificial synthetic ocular lens (IOL). This intervention is one of the most common ophthalmologic surgeries.

A very common problem—apart from the development of a so-called aftercaract or a secondary cataract, respectively—is that prior to the intervention, it is virtually impossible to select the lens to be implanted in a way as to avoid further, post-invasive vision corrections. Moreover, irregular wound healing and positioning errors of the artificial intraocular lens often cause visual defects such as myopia, hyperopia or astigmatism. Thus, it is in most cases impossible to exactly predict post-operative refraction following a cataract surgery. Amongst other things, this is due to the fact that the eye is a complex optical system, and some parameters required for such an assessment cannot be measured at all or only to a limited extent, such as the post-operative depth of the anterior chamber which is virtually impossible to determine prior to the intervention. Likewise, the determination of biometrical data of the eye to be operated, such as the radius of the cornea and the axis length, often gives rise to relatively large errors. Consequently, in approximately 83% of the patients, a value is currently obtained that deviates from the desired value by a maximum of plus/minus 1 dpt; in the remaining patients, this deviation is even greater. This deviation must then be corrected by additional corrective lenses such as glasses or a contact lens.

SUMMARY OF THE INVENTION

Thus, it was an object of the invention to provide artificial intraocular lenses that enable the desired refractive goal to be attained to the largest possible extent, thereby eliminating the need for additional corrective lenses.

This object is met in accordance with the invention by an artificial intraocular lens which is composed of a polymer material, wherein the polymer material contains photochemically active groups that enable the optical properties of the artificial intraocular lens to be changed by photoinduction.

The optical properties of the inventive intraocular lens, such as the refractive index, can be changed in a post-invasive procedure, thus allowing for a post-operative adjustment of the lens. This enables fine tuning to be performed by exposing the artificial intraocular lens to light, with the result that the patient will no longer be dependent on additional corrective lenses. Another advantage of the inventive artificial intraocular lens is that custom-made lens implants are no longer necessary, thus allowing for the use of standard lenses whose optical properties are then adjusted in a post-invasive procedure. Standard models could for example be available in different dioptric powers and different sizes, for example in steps of half a dioptre or a full dioptre.

Moreover, the artificial intraocular lens enables fine tuning to be performed after the healing process, thereby enabling an optimal vision to be attained.

The optical properties, in particular the optical imaging properties, of the inventive artificial intraocular lens may be changed by photoinduction, i.e. by exposure to light. This allows the lens to be adjusted in the eye upon implantation. Advantageously, the focal length of the lens or/and aspheric components are modified so as to obtain a high visual acuity.

The focal length of the lens may for example be altered by modifying the refractive index of the lens material.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
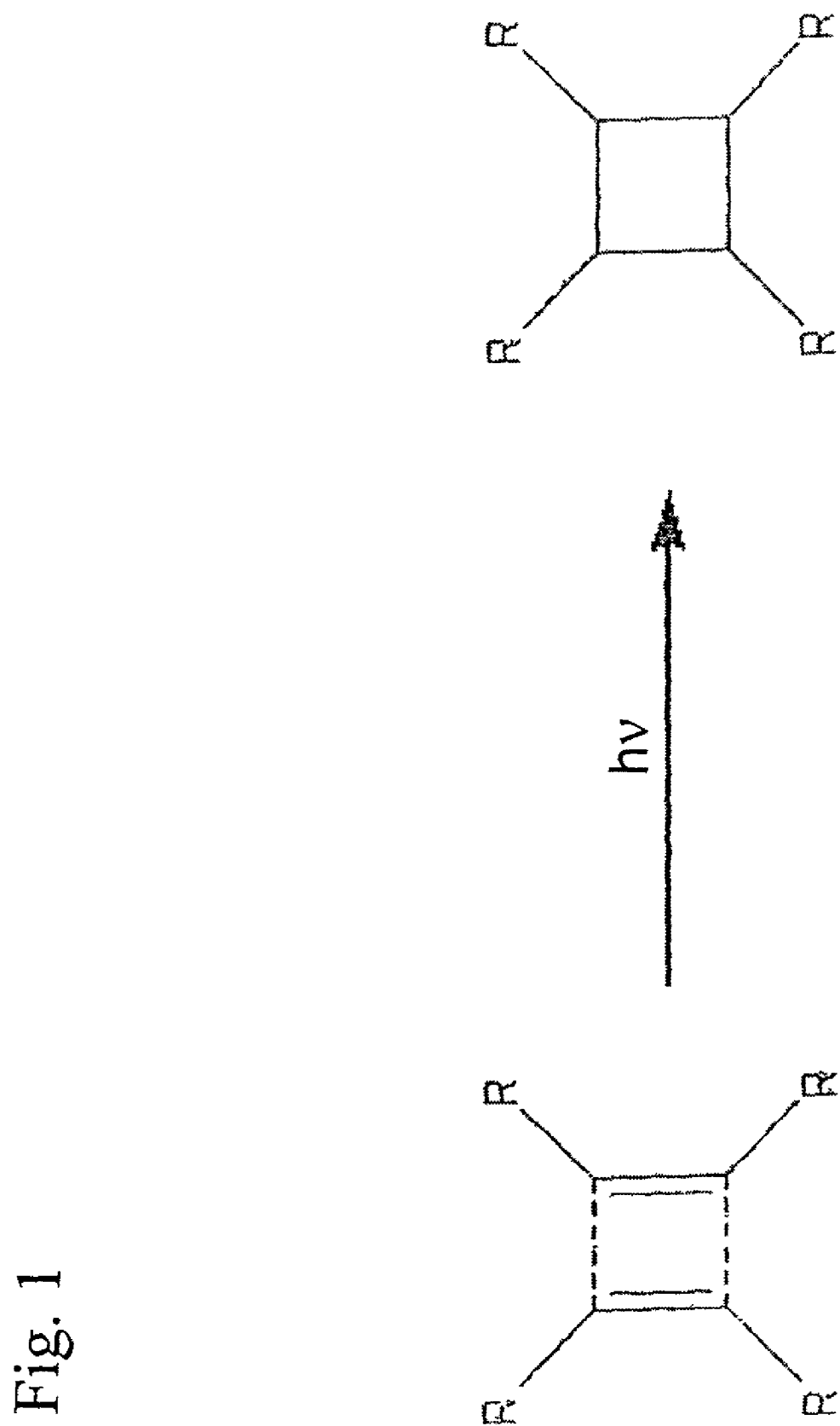
FIG. 1 is a schematic representation of the 2+2 cycloaddition resulting in the formation of a cyclobutane ring.
Figure 2:
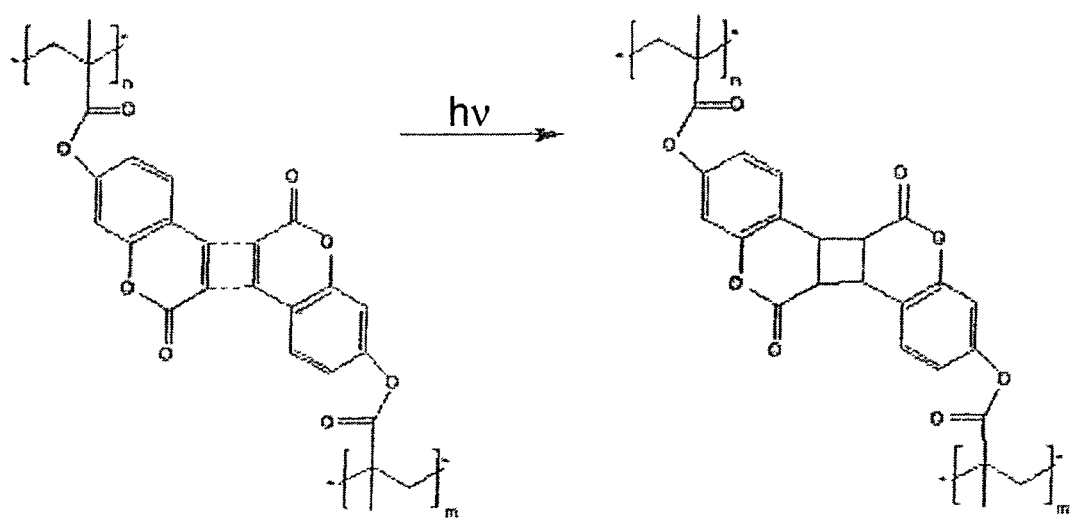
FIG. 2 is a schematic representation showing the structure of photodimers with coumarin side chains.
Figure 2:
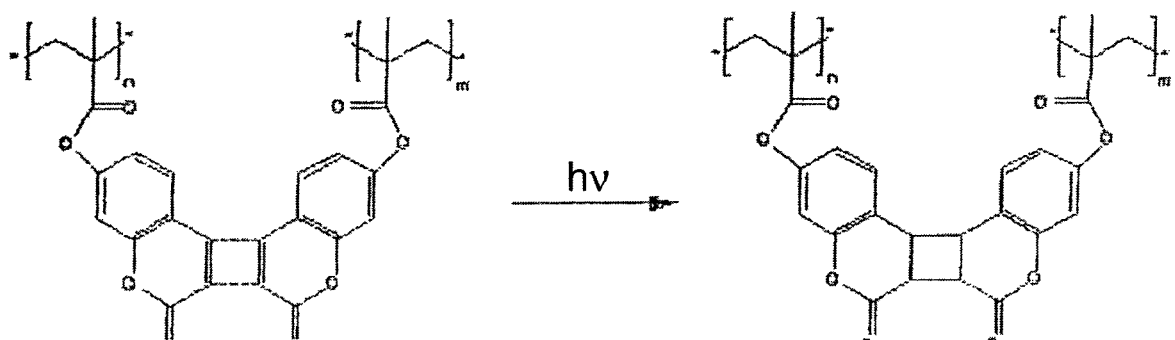
Figure 3:
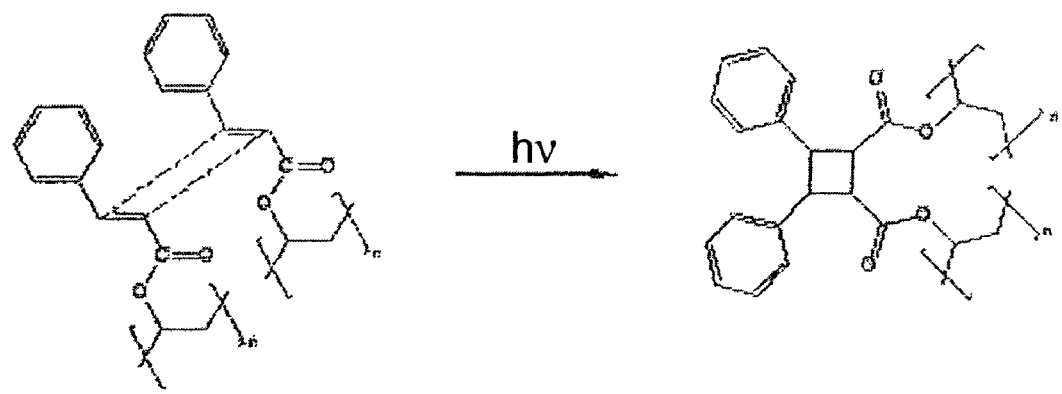
FIG. 3 is a schematic representation showing the structure of photodimers of poly(vinyl cinnamic acid ester).
Figure 3:
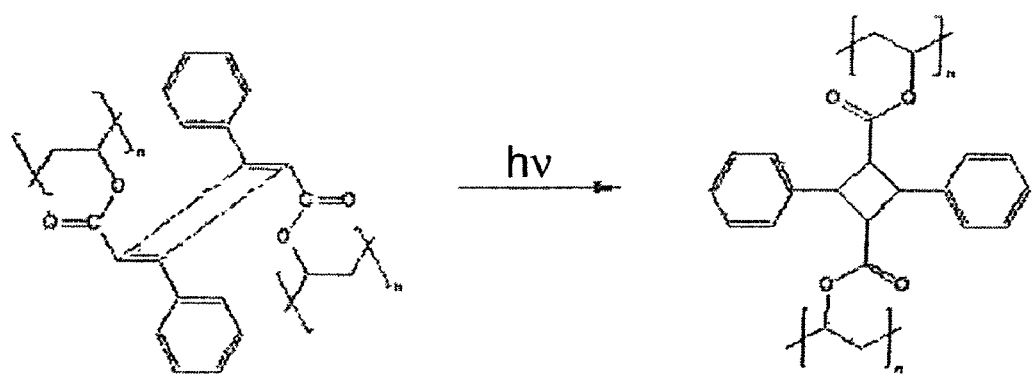

The inventive lens is formed of a polymer material which preferably fulfils some and, most suitably, all of the following requirements. First of all, it is of course essential for a lens material not to show any or no significant absorption in the visible spectral range. Moreover, the lens material must have a stable form at body temperature, i.e. in the range of approximately 35 to 45° C.

In order to provide for a technically simple and commercially favorable processing, however, the material must be capable of being processed in the molten state, which means that on the one hand, the glass transition temperature or the melting point, respectively, must exceed the body temperature; on the other hand, however, an excess temperatures must be avoided in order to ensure a problem-free processing.

Moreover, it is advantageous for the lens material to have a refractive index that is as high as possible, thereby allowing for the production of thinner lenses with less material.

Further advantageous properties include flexibility and a high water content or a high water permeability, respectively, of the lens material. The implantation of a flexible lens, which is rollable or foldable, requires a smaller incision than a rigid lens, thus providing for a more gentle surgical intervention. A lens with a high water permeability or water content, respectively, has the advantage that diffusion of nutrients dissolved in the eye liquid is not affected.

The inventive artificial ocular lens is preferably of a polymer material, selected from acrylic polymers, methacrylic polymers or silicone elastomers.

The polymer materials used according to the invention contain photochemically active groups. When the intraocular lens is exposed to light, this results in a photoinduced change of the optical properties of the artificial intraocular lens. A preferred method for this purpose is changing the refractive index of the polymer material by photoinduction. In order to change the refractive index, a number of advantageously two carbon-carbon double bonds are dimerized to form a cyclobutane ring by means of a [2π+2π] cycloaddition under the effect of light. In case a residue of an aromatic π-system is attached to at least on of the C—C double bonds, polarizability in the direction of the double bond strongly decreases due to the fact that resonance with the π-system will no longer be possible upon dimerization. Dimerization or formation, respectively, of the cyclobutane ring thus causes the refractive index to decrease. This effect is even greater if two aromatic π-systems are bonded to the C—C double bond, thereby forming a conjugated system due to the dimerizable double bond. On the other hand, the refractive index can be increased by cleavage of a cyclobutane ring.

Particularly preferred photochemically active groups are coumarin groups, chalcones, cinnamic acid groups and/or cyclobutane groups.

Preferably, the photochemically active groups are covalently bonded to the polymeric material of the intraocular lens, in particular as side chains. It is however also possible to provide artificial intraocular lenses made of a polymer material containing molecules with photochemically active groups incorporated or embedded therein.

Artificial intraocular lenses based on polymethacrylic coumarins, polyacrylic coumarins, polymethacrylic cinnamic acid ester, polyacrylic cinnamic acid ester, polyvinyl cinnamic acid ester as well as silicones containing coumarin groups, cinnamic acid groups or/and cyclobutane groups that are covalently bonded thereto are particularly preferred.

A particularly preferred lens material is poly(7-methacryloyloxy coumarin) (PMAOC). Poly(7-methacryloyloxy coumarin) may be produced in accordance with known methods (see for example WO 96/10069 or U.S. Pat. No. 2,725,377). In a first reaction stage, 7-hydroxycoumarin is esterified with methacrylic acid chloride to form a reaction product which is then polymerized.

Another preferred material for the inventive intraocular lenses is poly(vinyl cinnamic acid ester) which may be obtained by a chemical reaction of poly(vinyl alcohol) with cinnamic acid chloride.

Another preferred lens material is poly(cinnamoyloxyethyl methacrylate) (PCEM) which is synthesized from hydroxyethyl and acrylate which are at first subject to free-radical polymerization to form a reaction product which is then esterified with cinnamic acid chloride.

The inventive lenses advantageously have a refractive index n of 1.3 to 2.0, preferably of 1.5 to 1.9, and more preferably of 1.6 to 1.8. The change of refractive index that is performable according to the invention amounts to 0.001 to 0.1, in particular 0.005 to 0.05, and more preferably up to 0.03. This change may result in a change in dioptric power that is perfectly sufficient for adjustment in terms of medically relevant cases. If, for example, the refractive index of a lens material of n=1.625 is changed to n'=1.605, this results in a change of the focal length in the aqueous humour (at an assumed refractive index of the aqueous humour of n=1.336, an anterior and a posterior radius of curvature of the lens r1 and r2=20 mm, a thickness of the lens center of 0.8 mm) of f=4.6 cm to f'=5.0 cm which corresponds to a change in dioptric power of 21.555 to 20.067. Thus in this case, a change in dioptric power of approximately 1.5 dpt is obtained.

In another preferred embodiment, a change of the focal length of the lens is obtained by structuring the surface of the artificial intraocular lens by photoinduction. In order to do so, only certain areas are provided with photochemically active groups, or only certain areas are exposed to light, thus allowing a photoreaction to occur in these areas only. Advantageously, an effect is obtained that resembles that of a Fresnel lens.

In another preferred embodiment, a change in shape of the intraocular lens is obtained by photoinduction, for example by changing the profile or by elastically deforming the lens in the photoreaction process. This may for example be obtained by photoinduced density changes of the polymeric lens material. Changing the density of the material may for example result in a change in thickness of certain areas of the lens, which consequently leads to a change in curvature.

The inventive intraocular lenses may be iris-fixated or anterior-chamber lenses; preferably, however, they are posterior-chamber lenses, which means the lenses are implanted into the eye, and are not placed on or inserted into the cornea. The thickness of the lenses usually amounts to 0.8 to 2.0 mm, wherein an optically active area having a diameter of approximately 5 to 7 mm is present within a total diameter of approximately 12 to 13 mm. The lenses allow visible light to pass through, and while a small amount of absorption in the range of 400 to 500, in particular 400 to 450 nm, is tolerable, an absorption in particular in this range and in a range of <400 nm may even be desired so as to provide protection against UV radiation.

According to the invention, the photoinduced change of the optical properties are performable on the implanted intraocular lens. This enables visual acuity to be subsequently adjusted upon implantation or as soon as the eye has recovered from an operation.

According to the invention, an intraocular lens is provided that already consists of a polymer material prior to implantation. Thus, there is no in-situ polymerization in the eye or implantation of a monomer material which is to be polymerized in the eye. The lens itself is in fact already formed in advance, and it is only the optical properties of the lens that are changed by photoinduction due to a photoreaction with photochemically active groups.

The photoinduced change of the optical properties preferably occurs by exposure to light covering specific spectral ranges. In one embodiment, light is irradiated that covers a spectral range of 200 nm to 1500 nm. When light in the UV range, in particular of 200 to 400 nm, is irradiated, the photoinduced change is preferably caused by a 1-photon absorption. In this case, the energy irradiated for example by means of a laser or a mercury vapor lamp (if necessary, certain wavelength ranges can be blocked out during this process) preferably amounts to approximately $\geq 0.05$ J cm$^{-2}$, in particular to $\geq 0.1$ J cm$^{-2}$, more preferably $\geq 0.2$ J cm$^{-2}$, and most preferably $\geq 0.3$ J cm$^{-2}$ and up to 10 J cm$^{-2}$, in particular up to 5 J cm$^{-2}$, more preferably up to 2.5 J cm$^{-2}$, even more preferably up to 2 J cm$^{-2}$, and most preferably up to 1 J cm$^{-2}$. In any case, the irradiated light energy is adjusted in a way as to induce a photoreaction of the photochemically active groups, in particular a formation or cleavage of cyclobutane as described above, whilst avoiding an ablation of the lens material. The irradiated energy can however also be adjusted in dependence on the amount of photochemically active groups the material is loaded with, the load preferably amounting to $\geqq 50\%$, $\geqq 70\%$, $\geqq 90\%$, and more preferably to $\geqq 95\%$ of the theoretical value in a covalent bonding situation.

In another preferred embodiment, photoinduction is caused by two-photon absorption or multiple-photon absorption. In this case, a wavelength is irradiated that is in the range of 400 to 1500 nm. In two-photon absorption, an energy density is used that is advantageously in the range of $\geqq 2$ kJ cm$^{-2}$, more preferably $\geqq 4$ kJ cm$^{-2}$, and even more preferably $\geqq 5$ kJ cm$^{-2}$ and up to 20 kJ cm$^{-2}$, more preferably up to 10 kJ cm$^{-2}$. Radiation is preferably pulsed by means of a laser, the energy density per pulse preferably amounting to $\geqq 50$ mJ cm$^{-2}$, more preferably $\geqq 100$ mJ cm$^{-2}$ and up to 300 mJ cm$^{-2}$, more preferably up to 200 mJ cm$^{-2}$. Likewise, energy is selected in a way as to induce the photochemical reaction whilst avoiding an ablation of the lens material.

In two-photon excitation, the wavelength is selected in a way that a single photon does not suffice to induce photochemical activation; in order to obtain the required level of energy, a second photon must be added to the molecule upon excitation. The photochemical reaction is advantageously induced by two photons of the same wavelength. Embodiments comprising two photons of different wavelengths may however also prove advantageous in many cases, said embodiments however requiring an increased amount of technical effort. Thus, a specific photon density must be provided for a two-photon absorption. Due to the fact that intraocular lenses are worn in the eye and are therefore exposed to light at all times, it is of course essential for the photochemical reaction not to be induced by daylight or sunlight but only if there is a higher photon density. Two-photon absorption by means of visible light is a simple way of transporting light through the cornea to the lens, wherein the photon density required to induce the photochemical activation must be higher than that provided by daylight or sunlight. The absorption of two photons results in a photochemical activation by UV energy whilst avoiding an unwanted activation by daylight due to the fact that the photon density of daylight is not sufficient for a two-photon excitation.

Another advantage of the inventive lenses is that the photoinduced changes of the optical properties may be performed gradually and/or reversibly. Thus in a first stage, a partial change in refractive index can be obtained by gradual exposure to energy, followed by a subsequent adjustment as soon as the eye has completely recovered. Moreover, it is also possible to fine-tune visual acuity in a gradual manner. Moreover, the refractive index may be selectively increased or reduced, respectively, by systematic cleavage or formation of cyclobutane groups via exposure to the wavelength that is suitable for the particular process, thereby causing a change in the range of +dpt or -dpt, respectively.

Moreover, the invention relates to a method for producing an inventive artificial intraocular lens as described above, wherein a polymeric material containing photochemically active groups is provided in a first stage, said polymeric material then being used to form the lens.

In another particularly preferred embodiment, at least one area of the polymer material that is used to form the inventive artificial intraocular lens contains a chemical component in an immobilized form from which a pharmaceutical agent is releasable by photochemical activation. The agent has for example an antibiotic, anti-inflammatory, antimicrobial, antiviral, fungicidal, and especially a cytocital effect. The agent is preferably a corticosteroid, a non-steroidal anti-inflammatory agent, an anti-fibroblast growth factor or/and an agent that inhibits proliferative vitreoretinopathy or tissue fibrosis. The agent may be covalently bonded to the polymeric material, for example by means of photochemically cleavable linker molecules, wherein linker molecules from the group comprising cinnamic acid, coumarin and derivates are particularly preferred. The agent or an agent precursor may also be incorporated or embedded in the polymeric material. The agent is released by exposure to light, in particular by one-photon absorption and, even more preferred, by two-photon absorption. Lenses being loaded with an agent and the photoinduced release of this agent are described in detail in WO 01735867, for example.

Loading the inventive lenses with an agent that is releasable by photoinduction not only allows vision to be adjusted upon implantation by exposure to light but also enables a secondary cataract or an aftercataract to be treated by exposure to light.

While specific embodiments of the invention have been shown and described in detail to illustrate the application of the principles of the invention, it will be understood that the invention may be embodied otherwise without departing from such principles.

EXAMPLES

Example 1

Poly(7-methacryloyloxy coumarin) (PMAOC)

The synthesis of poly(7-methacryloyloxy coumarin) was performed by esterification of 7-hydroxy coumarin with methacrylic acid chloride to form a reaction product which was subsequently subject to free-radical polymerization in solution. The polymer shows no significant absorption in the visible spectral range, i.e. at wavelengths between 400 and 800 nm, and therefore appears to be transparent.

For examining the change in refractive index of PMAOC, a film containing an amount of 2 wt % of the polymer dissolved in chloroform was produced by spin coating (2000 rpm for 20 sec). A film with a film thickness of 180+/-4 nm was obtained. The film was exposed to UV light at a wavelength of 313 nm up to a maximum irradiation dose of 2.7 J cm$^{-2}$, the light being separated from the spectrum of a mercury vapor lamp by means of an interference filter. The refractive index was determined by ellipsometry, amounting to 1.804+/-0.007 prior to irradiation. The maximum change of refractive index amounted to 0.034+/-0.009.

It became apparent from UV/vis spectra of PMAOC upon exposure to different doses of a wavelength of 313 nm that at an energy density of 1.63 J cm-2, approximately 15% of the coumarin groups were dimerized.

Example 2

Poly(vinyl cinnamic acid ester) (PVCi)

Poly(vinyl cinnamic acid ester) may be obtained by a reaction of poly(vinyl alcohol) with cinnamic acid chloride, wherein a poly(vinyl cinnamic acid ester) with a degree of esterification of 95% according to $^1$H-NMR data was used. The material is substantially transparent but has an absorption at the short-wave end of the visible spectrum at approximately 400 to 450 nm, causing the material to appear slightly yellowish. This does not affect the use of the material as an eye lens, however, since the human brain gets used to a yellowish lens rather quickly, with the result that the lens is no longer perceived as being tinted. Moreover, the high increase in optical density below 400 nm is advantageous since it protects the eye from harmful UV radiation.

For examining the change of the refractive index of PVCi, a film containing an amount of 8 wt % of the polymer dissolved in diethylene glycol dimethyl ester was produced by spin coating (3000 rpm for 20 sec). The resulting film thickness amounted to 292+/−4 nm. The film was exposed to UV light at a wavelength of 266 nm up to a maximum irradiation dose of 2.8 J cm$^{-2}$. The refractive index was determined by ellipsometry, amounting to 1.590+/−0.003 prior to exposure. A maximum change in refractive index Δn of 0.048+/−0.004 was determined.

By examining UV/vis spectra, it was determined that a maximum change in refractive index is obtained when approximately 70% of the cinnamic acid molecules are dimerized.

The invention claimed is:

1. An artificial intraocular lens, comprising:
an artificial intraocular lens structure formed of a polymer material, said polymer material containing photochemically active groups so as to enable a photoinduced change of the optical properties of the artificial intraocular lens, wherein the photoinduced change of the optical properties is caused by at least one of two-photon absorption and multiple-photon absorption, said photoinduced changes of the optical properties being performed in a reversible manner.

2. An artificial intraocular lens according to claim 1, wherein the optical properties that are changeable are optical imaging properties.

3. An artificial intraocular lens according to claim 1, wherein at least one of focal length and aspheric components are changeable by photochemical processes.

4. An artificial intraocular lens according to claim 1, wherein the refractive index of the polymer material is changeable by photoinduction.

5. An artificial intraocular lens according to claim 1, wherein a structuring of a surface of the artificial intraocular lens is obtainable by photoinduction.

6. An artificial intraocular lens according to claim 1, wherein a density of the polymer material is changeable by photoinduction.

7. An artificial intraocular lens according to claim 1, wherein a change of a shape of the intraocular lens is obtainable by photoinduction.

8. An artificial intraocular lens according to claim 7, wherein a radius of curvature of at least one of one and both surfaces is changed.

9. An artificial intraocular lens according to claim 1, wherein the photoinduced change of the optical properties is performable on the implanted intraocular lens.

10. An artificial intraocular lens according to claim 1, wherein the lens material comprises groups of at least one of coumarin, cinnamic acid, chalcone and cyclobutane.

11. An artificial intraocular lens according to claim 1, wherein the photoinduced changes of the optical properties are performable in a gradual manner.

12. An artificial intraocular lens according to claim 1, wherein photochemically active groups that cause a photoinduced change of the optical properties of the artificial intraocular lens are covalently bonded to the polymeric material of the intraocular lens.

13. An artificial intraocular lens according to claim 1, wherein molecules comprising photochemically active groups that may cause a photoinduced change of the optical properties of the intraocular lens material are embedded in the polymeric material of the lens.

14. An artificial intraocular lens according to claim 1, wherein the photoinduced change of the optical properties is caused by exposure to light in a spectral range of 200 nm to 1500 nm.

15. An artificial intraocular lens according to claim 1, wherein the photoinduced change of the optical properties is caused by exposure to light of an intensity of greater than or equal to 0.1 J cm$^{-2}$.

16. A method for producing an artificial intraocular lens, the method comprising the steps of:
providing a polymeric material that contains photochemically active groups which may cause a photoinduced change of the optical properties of the lens material by at least one of two-photon absorption and multiple-photon absorption, wherein said photoinduced changes of the optical properties are reversible; and
forming an artificial intraocular lens of said polymeric material.

17. An artificial intraocular lens, comprising:
an artificial intraocular lens structure comprising a polymer material, said polymer material containing photochemically active groups, at least said photochemically active groups generating a photoinduced change of the optical properties of the artificial intraocular lens such that said photoinduced changes of the optical properties are reversible, wherein the photoinduced change of the optical properties is caused by at least one of two-photon absorption and multiple-photon absorption, said photochemically active groups being covalently bonded to said polymer material of said artificial intraocular lens structure.

* * * * *